(12) United States Patent
Frace et al.

(10) Patent No.: US 6,169,175 B1
(45) Date of Patent: *Jan. 2, 2001

(54) PREPARATION AND USE OF RECOMBINANT INFLUENZA A VIRUS M2 CONSTRUCT VACCINES

(75) Inventors: A. Michael Frace; Alexander I. Klimov; Jacqueline M. Katz, all of Atlanta, GA (US)

(73) Assignee: Centers For Disease Control and Prevention, Atlanta, GA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/906,930

(22) Filed: Aug. 6, 1997

(51) Int. Cl.$^7$ .................. C07H 21/04; A61K 39/145; C12P 21/06; C12N 1/20
(52) U.S. Cl. ............... 536/23.72; 424/9.34; 424/209.1; 435/69.3; 435/252.33; 435/325; 435/320.1
(58) Field of Search ............... 536/23.72; 435/69.3, 435/252.33, 325, 320.1; 424/9.34, 209.1

(56) References Cited

FOREIGN PATENT DOCUMENTS

WO 93/03173    2/1993 (WO).

OTHER PUBLICATIONS

Banerji et al., (1983) *Cell*, vol. 33, p. 729.
Black et al., (1993) *Journal of General Virology*, vol. 74, pp. 1673–1677.
Black et al., (1993) *Journal of General Virology*, vol. 74, pp. 143–146.
Bolivar et al., (1977) *Gene*, vol. 2, p. 95.
Brophy et al., (1994) *Experimental Parasitology*, vol. 79, pp. 89–96.
Brown et al., (1979) *Methods in Enzymology*, Academic Press, N.Y. vol. 68, pp. 109–151.
Chang et al., (1978) *Nature*, vol. 275, p. 617.
Ciampor et al., (1992b) *Virus Research*, vol. 22, pp. 247–258.
Epstein et al., (1993) *Journal of Immunology*, vol. 150, pp. 5484–5493.
Fiers et al., (1978) *Nature*, vol. 273, p. 113.
Fikrig et al., (1990) *Science*, vol. 250, pp. 553–555.
Frangioni et al., (1993) *Analytical Biochemistry*, vol. 210, pp. 179–187.
Geoddel et al., (1979) *Nature*, vol. 281, p. 544.
Graham et al., (1977) *J. Gen. Virol.* vol. 36, pp. 59–72.
Harrison et al., (1977) *Virology*, vol. 77, pp. 319–329.
Graham et al., (1977) *Virology*, vol. 86, pp. 10–21.
Grambas et al., (1992) *Virology*, vol. 190, pp. 11–18.
Grambas et al., (1992) *Virology*, vol. 191, pp. 541–549.
Guinea et al., (1994) *FEBS Letter*, vol. 343, pp. 242–246.
Holsinger et al., (1995) *Journal of Virology*, vol. 69, pp. 1219–1225.

(List continued on next page.)

*Primary Examiner*—Hankyel Park
(74) *Attorney, Agent, or Firm*—McDonnell Boehnen Hulbert & Berghoff (57) ABSTRACT

The present invention provides a method of increasing the recombinant expression and solubility of influenza A virus M2 polypeptide comprising nucleic acids encoding variants of the M2 protein of influenza A virus in which transmembrane and other hydrophobic domains have been deleted. The present invention also provides purified polypeptides encoded by the nucleic acids, which polypeptides are immunogenic and are less hydrophobic than full-length M2. Also provided are vaccines comprising variants of M2 expressed in prokaryotic hosts. Further provided are methods of preventing influenza A infection using vaccines comprised of variants of M2. Also provided are antibodies raised against the variants of M2, and use of such antibodies in diagnosis and treatment of influenza A infections.

8 Claims, 4 Drawing Sheets

OTHER PUBLICATIONS

Holsinger et al., (1994) *Journal of Virology*, vol. 68, pp. 1551–1563.
Hughey et al., (1995) *Virology*, vol. 212, pp. 411–421.
Ito et al., (1991) *Journal of Virology*, vol. 65, pp. 5491–5498.
Jacob et al., (1985) *Embo Journal*, vol. 4, pp. 3339–3343.
Jakeman et al., (1989) *Journal of General Virology*, vol. 70, pp. 1523–1531.
Johnson et al., (1989) *Nature*, vol. 338, pp. 585–587.
Jones, (1977) *Genetics*, vol. 85, p. 23.
Katz et al., (1996) *Options for the Control if Influenza III*, pp. 837–843.
Kingsman et al., (1979) *Gene*, vol. 7, p. 141.
Kleid et al., (1981) *Science*, vol. 214, pp. 1125–1129.
Lamb et al., (1985) *Cell*, vol. 40, pp. 627–633.
Ling et al., (1994) *Parasite Immunology*, vol. 16, pp. 63–67.
Lusky et al., (1983) *Mol. Cell. Bio.*, vol. 3, p. 1108.
MacIntyre et al., (1987) *J. Biol. Chem.*, vol. 262, pp. 8416–8422.
Mulligan et al., (1980) *Science*, vol. 209, p. 1422.
Osborne et al., (1984) *Moll. Cell. Bio.*, vol. 4, p. 1293.
Shimbo et al., (1996) *Biophysical Journal*, vol. 70, pp. 1335–1346.
Slepushkin et al., (1995) *Vaccine*, vol. 13, pp. 1399–1402.
Smith et al., (1988) *Gene*, vol. 67, pp. 31–40.
Southern, et al., (1982) *J. Molec. Appl. Genet.*, vol. 1, p. 327.
Stinchcomb et al., (1979) *Nature*, vol. 282, p. 39.
Srivastava et al., (1991) *Microbiological Immunology*, vol. 35, pp. 863–870.
Srivastava et al., (1995) *Vaccine*, vol. 13, pp. 1251–1258.
Sugden et al., (1985) *Mol. Cell Biol.*, vol. 5, pp. 410–413.
Sugrue et al., (1990) *EMBO Journal*, vol. 9, pp. 3469–3476.
Summers et al., (1989) *J. Biol. Chem.*, vol. 264, pp. 20082–20088.
Tosteson et al., (1994) *Journal of Membrane Biology*, vol. 142, pp. 117–126.
Treanor et al., (1990) *Journal of Virology*, vol. 64, pp. 1375–1377.
Tschemper et al., (1980) *Gene*, vol. 10, p. 157.
Von Heijne et al., (1990) *J. Membrane Biol.*, vol. 115, pp. 195–201.
Wang et al., (1995) *Biophysical Journal*, vol. 69, pp. 1363–1371.
Wang et al., (1994) *Virology*, vol. 205, pp. 133–140.
Yamane et al., (1988) *J. Biol. Chem.*, vol. 263, pp. 19690–19696.
Zebedee et al., (1988) *Journal of Virolgy*, vol. 62, pp. 2762–2772.

PREPARATION AND USE OF RECOMBINANT INFLUENZA A VIRUS M2 CONSTRUCT VACCINES

BACKGROUND OF THE INVENTION

The prior art illustrates the current strategy for control of influenza by yearly vaccination with whole-virus or subunit vaccines. The currently-licensed vaccines are designed to stimulate neutralizing antibodies against hemagglutinin (HA) and/or neuraminidase (NA), the major surface antigens of the influenza virus. However, due to frequent and unpredictable structural variation of HA and NA, influenza vaccines must be seasonally customized to circulating virus strains, a process which is deficient in providing protective immunity against all but closely matched viral strains.

There is a need for a vaccine subunit component capable of inducing broader, more cross-reactive immunity to type A influenza viruses. One such component may be M2, a structurally conserved influenza A viral surface protein (Slepushkin et al., 1995; to et al., 1991). Antibody to M2 has been shown to restrict influenza virus replication in cell culture and in infected mice (Zebedee and Lamb (1988) and Treanor et al., (1990). Full length M2 expressed in baculovirus has been shown to raise serum titers and stimulate T-cell responses in immunized animals (Katz, et al, 1996). Further, vaccination of mice with recombinant full-length M2 has been shown to enhance viral clearance from infected lungs and to provide protection from lethal challenge with heterologous influenza A virus (Slepushkin et al., 1995).

Since M2 is not expressed to any extent in virions (Zebedee & Lamb, 1988), the current whole virus or split-product influenza vaccine contains only minimal amounts of M2. To be useful as a component of a vaccine, M2 must be expressed and purified as a recombinant product. However, expression of full-length M2 has been shown to be detrimental to cell culture in prokaryotic and eukaryotic expression systems (Guinea and Carrasco, 1996; Black et al., 1993). To date, expression of sufficient quantities of recombinant M2 for use in experimental studies can only be accomplished by culturing eukaryotic host cells in the presence of the irreversible M2 inhibitor, amantadine.

Wholly apart from the challenges in expression of recombinant M2, the hydrophobic nature of full-length M2 compromises the yield and purity of M2 preparations and necessitates the use of detergents or other agents to maintain M2 in a soluble form. Certain such solubilizing agents are not desirable constituents of vaccine formulations. The present invention solves this shortcoming in the prior art by providing a variant M2 protein with reduced hydrophobicity and concomitantly enhanced solubility characteristics relative to full-length M2.

SUMMARY OF THE INVENTION

The present invention solves the problems of the prior art approaches to recombinant M2 production by providing new recombinant forms of M2 whose structure has been modified to allow simple prokaryotic expression as a soluble, readily purified variant protein which retains antigenic and immunogenic properties. A preferred embodiment of the present invention involves a recombinant construct in which the entire or a significant portion of the transmembrane domain has been deleted. Alternatively, residues within the transmembrane domain may simply be altered, for example by substitution of hydrophilic or neutral amino acid residues for hydrophobic residues in such a way as to inactivate the ion channel activity of the variant M2 polypeptide. Additional hydrophobic residues may also be deleted, resulting in a less hydrophobic molecule which can be readily solubilized and efficiently purified. The present invention further relates to vaccines comprised of these new recombinant forms of M2, and to methods of prevention and treatment of influenza A virus infections.

Other objects, features and advantages of the present invention will become apparent more fully by the following description.

Further, the present invention can more fully be understood from the following description in conjunction with the accompanying drawings in which:

DETAILED DESCRIPTION OF THE INVENTION

The present invention provides for the modification of M2 whereby hydrophobic residues within M2 are deleted, thereby rendering the protein soluble and in a form suitable for high-yield expression and purification. Constructs involving deletion of the entire transmembrane domain (sM2/G) or deletion of the transmembrane region and 12 appended residues (ssM2/G) were prepared.

The following examples merely illustrate the best mode now contemplated for practicing the invention, but should not be construed to limit the invention. All literature citations herein are expressly incorporated by reference.

EXAMPLE 1

PCR and Plasmid Construction

Figure 1:
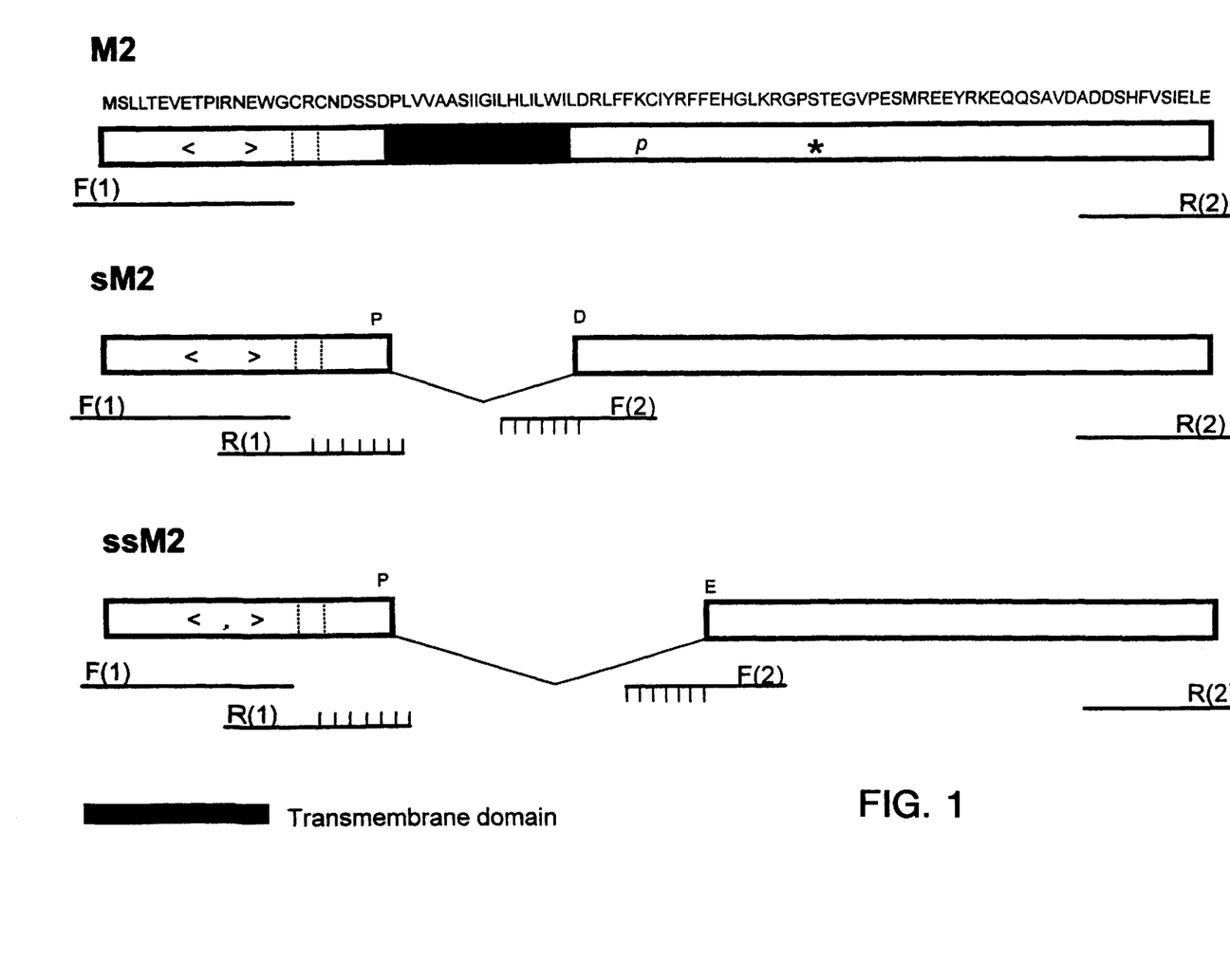
FIG. 1 is a schematic diagram of M2 and deletion constructs sM2 and ssM2.

Full length and truncated forms of M2 cDNA were made by PCR from RNA of A/Aichi/2/68 (H3N2) virus. FIG. 1 shows schematic diagrams of M2 and the deletion constructs sM2 and ssM2. Each diagram shows a boxed diagram of the M2 structure and the area deleted. Below each are the oligonucleotide primer positions used in constructing the cDNAs. F(1) is forward primer 1, F(2) forward primer 2, R(1) reverse primer 1, (R2) reverse primer 2. (A) The M2 amino acid sequence is represented in three boxes, an extracellular domain, a darkened transmembrane domain, and an intracellular domain. Notations within these boxes include epitopes or posttranslational modifications which have been described for M2: (<>) epitope for Mab 14C2; vertical dashed lines are cysteine sulfhydryl linkages; (p) is a palmitoylation site; and (*) is a phosphorylation site. (B) sM2 shows a deletion between Pro(25) and Asp(44). The deletion is performed with primer annealment indicated with vertical lines. (C) ssM2 has a deletion from Pro(25) to Glu(56).

Four oligonucleotide primers were designed to generate cDNA. Forward-1 primer (3'CCCGAATTCTTATGAGCCTTCTAACCGAGGTCG AAACGC CTATCAGAAACGAATGGGGATGC5' SEQ. ID NO. 1) was specific for the 5' coding region of the M2 gene (nucleotides 1–51) and began with a 5' EcoR1 restriction site. The reverse-1 primer (5'GTCTTTGCTTACCCCTACGTCTACGTTGCTAAGT TCACTAGGACCTCCTCCC3' SEQ. ID NO. 2) coded for 3' amplification from nucleotide 75. The forward-2 primer (sM2, 5'CAAGTGATCCTG GAGGAGGAGATC GTCTCTTCTTCAAATGC3' SEQ ID NO. 3; ssM2, 5'CAAGTGATCCTGGAGGAGGA AAACACGGTCT-GAAAAGAGGGCC3' SEQ ID NO. 3) was varied to flank areas chosen for deletion and contained a 5' region homologous to the reverse-1 primer to allow annealment. These primers also coded for three glycine residues inserted in place of the deleted segments. The reverse-2 primer (3'CTATCAGTAAAGCAGTCGTATCTCGACCTCATC AGCTGCCC5' SEQ ID NO. 5) coded for the 3' end of M2 and provided a 3' Sal1 restriction site. Full-length M2 cDNA was prepared by RT-PCR using forward-1 and reverse-2 primers. For deletion constructs, '5' side' and '3' side' reactions were carried out, annealed, then amplified to produce full length M2 or deletion cDNAs. These were digested with EcoR1 and Sal1, purified by gel electrophoresis and ligated into EcoR1 and Sal1 sites of a plasmid vector, pGEX-5$_a$ (Pharmacia, Piscataway, N.J.). The construct which has been designated sM2 has a deletion between amino acids 25 and 44 of native M2. The construct designated ssM2 has a deletion between amino acids 25 and 56 of native M2. Plasmids were transformed into competent *E. coli* strain JM109 (Stratagene, La Jolla, Calif.). Plasmid sequences were verified by automated nucleotide sequence analysis using standard protocols.

The teachings set forth in Example 1 is meant to be illustrative rather than limiting. Those skilled in the art will recognize that variant M2 polypeptides of the present invention may be produced by any one of a variety of recombinant methods. The basic steps in the recombinant production of variant M2 polypeptides include:

a) construction of a synthetic or semi-synthetic DNA encoding the variant M2 polypeptide, b) integrating said DNA into an expression vector in a manner suitable for the expression of the variant M2 polypeptide either alone or as a fusion protein, c) transforming an appropriate eukaryotic or prokaryotic host cell with said expression vector, d) culturing said transformed or transfected host cell, and e) recovering and purifying the recombinantly produced variant M2 polypeptides.

For recombinant expression, the variant M2 coding sequence may be wholly synthetic, semi-synthetic or the result of modification of the native M2 gene sequence.

Synthetic genes, the in vitro or in vivo transcription and translation of which will result in the production of variant M2 polypeptides may be constructed by techniques well known in the art. Owing to the natural degeneracy of the genetic code, the skilled artisan will recognize that a sizable yet definite number of DNA sequences may be constructed which encode variant M2 polypeptides. The gene encoding the variant M2 polypeptides may be constructed by synthetic methodology. Such methodology of synthetic gene construction is well known in the art. The DNA sequence corresponding to the variant M2 polypeptide genes may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

The DNA sequences of the M2 genes of numerous influenza A viruses are known (to et al., 1991). M2 is thought to provide an obligatory transmembrane proton flux for viral replication (Sugrue et al., 1990; Ciampor et al., 1992b; Grambas and Hay, 1992). As a membrane transport protein, M2 functions as an open pore which conducts cations in a nonselective manner (Tosteson et al., 1994; Shimbo et al., 1996). This conductance is thought to permeabilize host cells expressing recombinant M2, and may explain difficulties that others have had in achieving high levels of recombinant M2 expression in prokaryotic as well as eukaryotic systems (Guinea and Carrasco, 1996; Black et al., 1993). For the purposes of this invention, the transmembrane region of M2 is defined generally as that portion of the M2 polypeptide which spans all or part of the lipid bilayer of the influenza A virus surface. In the examples provided herein, residues 25–43 of the native M2 of the A/Aichi/2/68 (H3N2) virus correspond to the transmembrane region. Those skilled in the art will appreciate that comparable regions of other influenza A viruses and newly emerging influenza A viruses will correspond to this general description of a transmembrane region and the present invention contemplates removal or alteration of sufficient residues within the transmembrane region to render said region functionally inactive and, preferably, to reduce overall hydrophobicity, thereby allowing for efficient expression and purification of variant M2 polypeptides following culture in prokaryotic and eukaryotic hosts.

Vector Construction Generally

Construction of suitable vectors containing the desired coding and control sequences employ standard ligation techniques. Isolated plasmids or DNA fragments are cleaved, tailored, and religated in the form desired to form the plasmids required.

To effect the translation of the variant M2 polypeptides, one inserts the engineered variant M2 DNA coding sequence in any of a plethora of appropriate recombinant DNA expression vectors through the use of appropriate restriction endonucleases. A synthetic variant M2 coding sequence is designed to possess restriction endonuclease cleavage sites at either end of the transcript to facilitate isolation from and integration into these expression and amplification and expression plasmids. The coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the variant M2 coding sequence with control sequences to achieve proper in-frame reading and expression of the variant M2 polypeptide genes.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species Bolivar, et al., 1977. pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

The variant M2 polypeptide coding sequence must be positioned so as to be in proper reading frame with the promoter and ribosome binding site of the expression vector, both of which are functional in the host cell in which the variant M2 polypeptide is to be expressed. In the preferred practice of the invention, the promoter-operator region is placed in the same sequential orientation with respect to the ATG start codon of DNA sequence encoding the variant M2 polypeptide as the promoter-operator occupies with respect to the ATG-start codon of the gene from which it was derived. Synthetic or modified promoter-operator regions such as the tac promoter are well known in the art. When employing such synthetic or modified promoter-operator regions they should be oriented with respect to the ATG start codon of the variant M2 polypeptide coding sequence as directed by their creators.

Specifics for Prokaryotic Expression

In general, prokaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537), *E. coli* W3110 (prototrophic, ATCC No. 27325), bacilli such as *Bacillus subtilis*, and other enterobacteriaceae such as *Salmonella typhimurium* or *Serratia marcescans*, and various pseudomonas species may be used. Promoters suitable for use with prokaryotic hosts include the b-lactamase (vector pGX2907 [ATCC 39344] contains the replicon and b-lactamase gene) and lactose promoter systems (Chang et al., 1978; Goeddel et al., 1979), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding variant M2 polypeptides using linkers or adapters to supply any required restriction sites. Promoters for use in bacterial systems also will contain a Shine-Dalgarno sequence operably linked to the DNA encoding variant M2 polypeptides. These examples are illustrative rather than limiting.

Fusion Proteins

The variant M2 polypeptides may be made either by direct expression or as fusion protein comprising the variant M2 polypeptide followed by enzymatic or chemical cleavage. It is often observed in the production of certain peptides in recombinant systems that expression as a fusion protein prolongs the lifespan and/or increases the yield of the desired peptide. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P. (1990).

Therefore, it may be desirable to fuse the coding sequence of a particular variant M2 polypeptide in-frame to a larger gene coding sequence resulting in the production of a fusion protein.

Eukaryotic Expression

The variant M2 polypeptides may also be recombinantly produced in eukaryotic expression systems.

Eukaryotic Signal Peptides: An advantage of eukaryotic expression systems is that it is possible to obtain a secreted protein product. If such a result is desired, it is necessary to modify the coding sequence of the variant M2 polypeptide to incorporate a translated signal peptide encoding sequence. Generally, signal peptides are proteolytically cleaved from a residual protein as part of the secretory process in which the protein is transported into the host cell periplasm or culture medium.

It is well known in the art that signal peptides facilitate the extracellular discharge of secretory proteins in both prokaryotic and eukaryotic environments. It has been shown that the addition of a heterologous signal peptide to a normally cytosolic protein will result in the extracellular transport of the normally cytosolic protein in *E. coli*. (MacIntyre, et al., 1987). It is well known in the art that alternate signal peptide sequences may function with heterologous coding sequences. The recombinant production of such fusion proteins maybe accomplished by the addition of a DNA sequence encoding a signal peptide appropriate to the host organism inserted 5' to, and in reading frame with, the protein coding sequence.

Signal peptides are well known in the art which could be similarly incorporated into the variant M2 polypeptide structure. In the preferred practice of the invention the signal peptide used is a signal peptide native to a secretory protein of the host cell line. Furthermore, the signal sequence may be wholly synthetic. Synthetic "idealized" signal peptides have been shown to function in both prokaryotic and eukaryotic environments. (von Heijne, G., 1990). The principles of signal peptides are similar in both prokaryotic and eukaryotic organisms. Both prokaryotic and eukaryotic signal peptides possess an overall three domain structure and with no precise sequence conservation necessary to preserve function. von Heijne, G., supra. Generally, the presence of basic and/or charged amino acid residues near the amino terminus of the structural protein inhibits secretion. (Yamane, K., et al., 1988; Summers, R. G., et al., 1989). In order to ensure the efficient cleavage of the signal peptide from the fusion protein construct, it is desirable to maintain the nature of the amino acid sequence at the interface between the signal peptide and the coding sequence of the mature art protein. Conservation of charge and hydrophobicity and the elimination of charged residues immediately downstream of the signal peptide cleavage point are generally important to efficient translocation. However, it is not critical that any one particular amino acid sequence be maintained.

Eukaryotic Promoters: Preferred promoters controlling transcription in mammalian host cells may be obtained from various sources, for example, the genomes of viruses such as: polyoma. Simian Virus 40 (SV40), adenovirus, retroviruses, hepatitis-B virus and most preferably cytomegalovirus, or from heterologous mammalian promoters, e.g. b-actin promoter. The early and late promoters of the SV40 virus are conveniently obtained as an SV40 restriction fragment which also contains the SV40 viral origin of replication. (Fiers, et al., 1978). The entire SV40 genome may be obtained from plasmid pBRSV, ATCC 45019. The immediate early promoter of the human cytomegalovirus may be obtained from plasmid pCMBb (ATCC 77177). Of course, promoters from the host cell or related species also are useful herein.

Eukaryotic Enhancers: Transcription of a DNA encoding variant M2 polypeptides by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (Laimins, L. et al., 1981) and 3' (Lusky, M. L., et al., 1983) to the transcription unit, within an intron (Banerji, J. L. et al., 1983) as well as within the coding sequence itself (Osborne, T. F., et al., 1984). Many enhancer sequences are now known from mammalian genes (globin, RSV, SV40, EMC, elastase, albumin, a-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Eukaryotic Expression Vectors: Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding variant M2 polypeptides. The 3' untranslated regions also include transcription termination sites.

Eukaryotic Selectable Markers: Expression vectors may contain a selection gene, also termed a selectable marker. Examples of suitable selectable markers for mammalian cells are dihydrofolate reductase (DHFR, which may be derived from the BglII/HindII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR⁻ cells (ATCC CRL-9096) and mouse LTK⁻ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., 1982), mycophenolic acid (Mulligan, R. C. and Berg, P. 1980) or hygromycin (Sugden, B. et al., 1985). The three examples given above employ bacterial genes under eukaryotic control to convey resistance to the appropriate drug G418 or neomycin (geneticin), xgpt (mycophenolic acid) or hygromycin, respectively.

Eukaryotic Host Cells: Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al. (1989). *Molecular Cloning: A Laboratory Manual*, Cold Spring Harbor Press, Cold Spring Harbor Laboratory, Cold Spring Harbor, N.Y. or *Current Protocols in Molecular Biology* (1989) and supplements.

Preferred suitable host cells for expressing the vectors of this invention encoding variant M2 polypeptides in higher eukaryotes include: African green monkey kidney line cell line transformed by SV40 (COS-7, ATCC CRL-1651); transformed human primary embryonal kidney cell line 293,(Graham, F. L. et al. 1977); baby hamster kidney cells (BHK-21(C-13), ATCC CCL-10); chinese hamster ovary cells CHO-DHFR$^-$ (ATCC CRL-9096), mouse Sertoli cells (TM4, ATCC CRL-1715); African green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

Yeast Expression

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example, (ATCC-40053, Stinchcomb, et al, 1979); Kingsman et al., 1979); Tschemper et al., 1980) is commonly used. This plasmid already contains the trp gene which provides a selectable marker for a mutant strain of yeast lacking the ability to grow in tryptophan, for example ATCC no. 44076 or PEP4-1 (Jones, 1977).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC 1 ATCC 39532), glyceraldehyde-3-phosphate dehydrogenase (derived from plasmid pHcGAPC1 ATCC 57090, 57091), *Zymomonas mobilis* (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from

*Saccharomyces cerevisiae* (found in conjuction with the CYC1 promoter on plasmid YEpsec-hI1beta ATCC 67024), also are advantageously used with yeast promoters.

Expression in Vaccinia

The variant M2 polypeptides may also be expressed in vaccinia virus.

Paoletti, et al. (U.S. Pat. Nos. 4,722,848 and 5,110,587) describe a general method wherein exogenous DNA sequences are introduced into nonessential regions of the vaccinia virus genome, thereby effecting expression of said exogenous sequences. Paoletti, et al. (U.S. Pat. No. 5,174,993) describes a method for inducing an immunological response in a mammal to a pathogen by incorporation of exogenous DNA sequences derived from the pathogen into avipox virus. The teachings of these patents are hereby incorporated in their entirety be reference. The method of these patents may readily be modified to incorporate variant M2 polypeptide sequences of the present invention.

Expression by Naked DNA

The variant M2 polypeptides may also be expressed in vivo using the "naked DNA" approach as described by Felgner, et al. (U.S. Pat. No. 5,589,466). This approach entails delivery (typically by injection) of isolated nucleic acids into mammalian tissue, resulting in transient expression of the injected nucleic acids. Transient expression of foreign genes in mammalian tissue invokes an immune response which can be protective. The teachings of this patent are hereby incorporated in their entirety by reference and may readily be modified for use with the variant M2 polypeptide sequences of the present invention.

EXAMPLE 2

Expression and Isolation of Fusion Protein

The pGEX vector (Pharmacia, Piscataway, N.J.) was chosen to express the constructs, and allows purification of the products with a simple affinity matrix. pGEX is designed to express, under control of the inducible tac promoter, glutathione S-transferase (GST; from *Schistosoma japonicum*) as a 29 kDa fusion to the N-terminus of a subcloned sequence (Smith and Johnson, 1988). The fusion protein can be purified from bacterial lysates by affinity chromatography using glutathione sepharose® 4B. The fusion product may also be separated by a site-specific protease, Factor Xa, whose site is immediately downstream of the C-terminus of the GST.

1. Soluble fusion proteins Cells were grown from frozen stocks in overnight cultures of Luria broth (LB) containing 100 vg/ml ampicillin. This culture was then diluted 1:10 the next morning and grown for 1.5 hr at 37° C. with vigorous shaking. IPTG (isopropyl β-D-thiogalactoside) was then added to a final concentration of 0.1 mM and incubation continued for 3–4 hrs. To monitor cell growth an aliquot of culture was taken every 0.5 hr after the initial dilution and cell density ($A_{600\ nm}$ was measured over the induction period. Cells were pelleted by centrifugation and resuspended in cold lysis buffer (50 Tris, 100 NaCl, 1 EDTA, pH 8.0). Lysozyme was added to 1 mg/ml and phenylmethyl-sulfonylfluoride (PMSF) added to a concentration of 0.5 mM. The suspension was kept on ice for 15 min. Dithiothreitol (DTT) was added to a concentration of 5 mM, and the suspension was lysed by sonication (probe-tip) on ice for 1 min. Triton X-100 was added to a concentration of 1% and the lysate was mixed gently for 0.5 hr. The lysate was then centrifuged at 12,000×g for 10 min at 4° C. The supernatant was decanted and added to a washed glutathione sepharose® (Pharmacia, Piscataway, N.J.) slurry (50% v/v in phosphate-buffered saline (PBS)), with the slurry volume being equal to 0.2% of the original bacterial culture volume. This mixture was gently stirred for 30 min. The sepharose® was then pelleted, the supernatant removed and discarded. The sepharose® was washed a minimum of three times in PBS. Fusion protein was eluted from the sepharose® pellet by addition of elution buffer (50 Tris, 10 reduced glutathione, pH 8.0) using a volume equal to the bed volume of sepharose®. The elution buffer/resin mixture was mixed for 15 min at room temperature, then pelleted at 500×g for 5 min. The supernatant was harvested and a second elution was performed for residual product.

To enzymatically cleave ssM2 from the GST moiety the fusion product was left bound to sepharose® and treated overnight with 10 vg of Factor Xa (New England Biolabs, Beverly, Mass.) at 4° C. The sepharose® with bound GST was spun down, and the supernatant, containing the released ssM2, was harvested.

2. Insoluble fusion proteins. The insoluble forms of M2 were isolated using the above protocol with the suggested additions of Frangioni and Neel (1993), which include: (1) introduction of 1.5% sarkosyl prior to sonication and (2) raising the concentration of Triton X-100 to 4%. PBS washes of the bound glutathione sepharose® and the elution buffer contained 0.1% Triton X-100.

EXAMPLE 3

Electrophoresis and Western Blotting

Figure 3A:
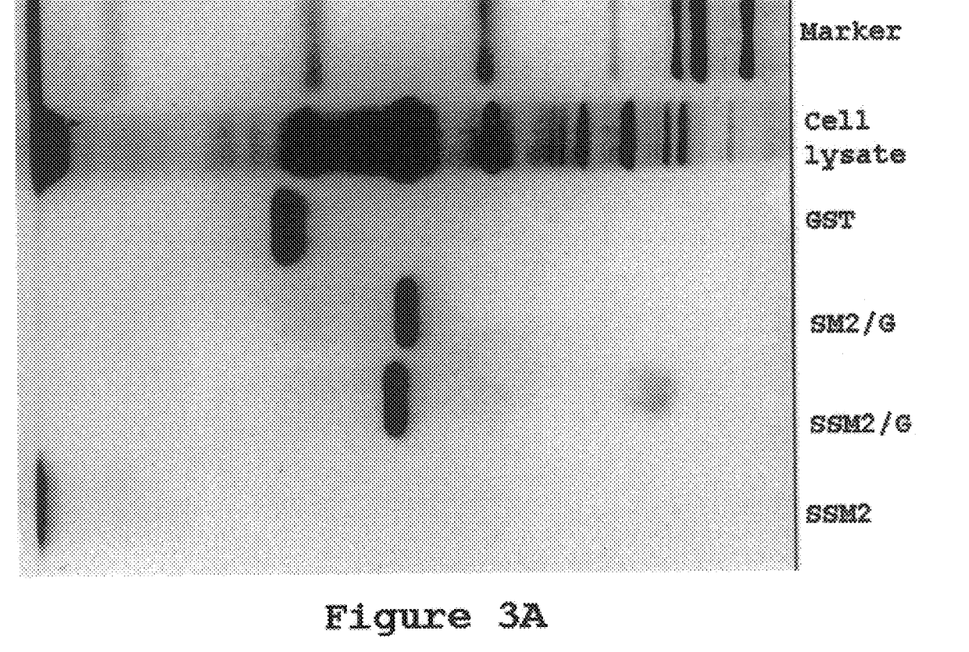
FIG. 3(A) is a coomassie-stained SDS-PAGE gel.
Figure 3B:
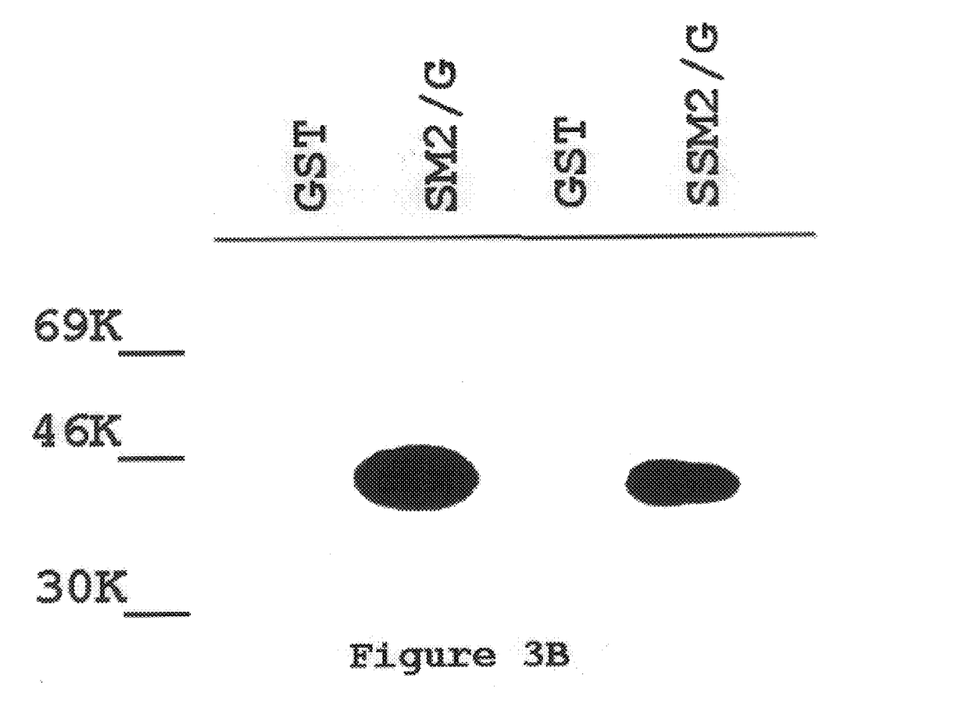
FIG. 3(B) is a Western blot of fusion proteins containing variant M2 polypeptides.
Figure 4:
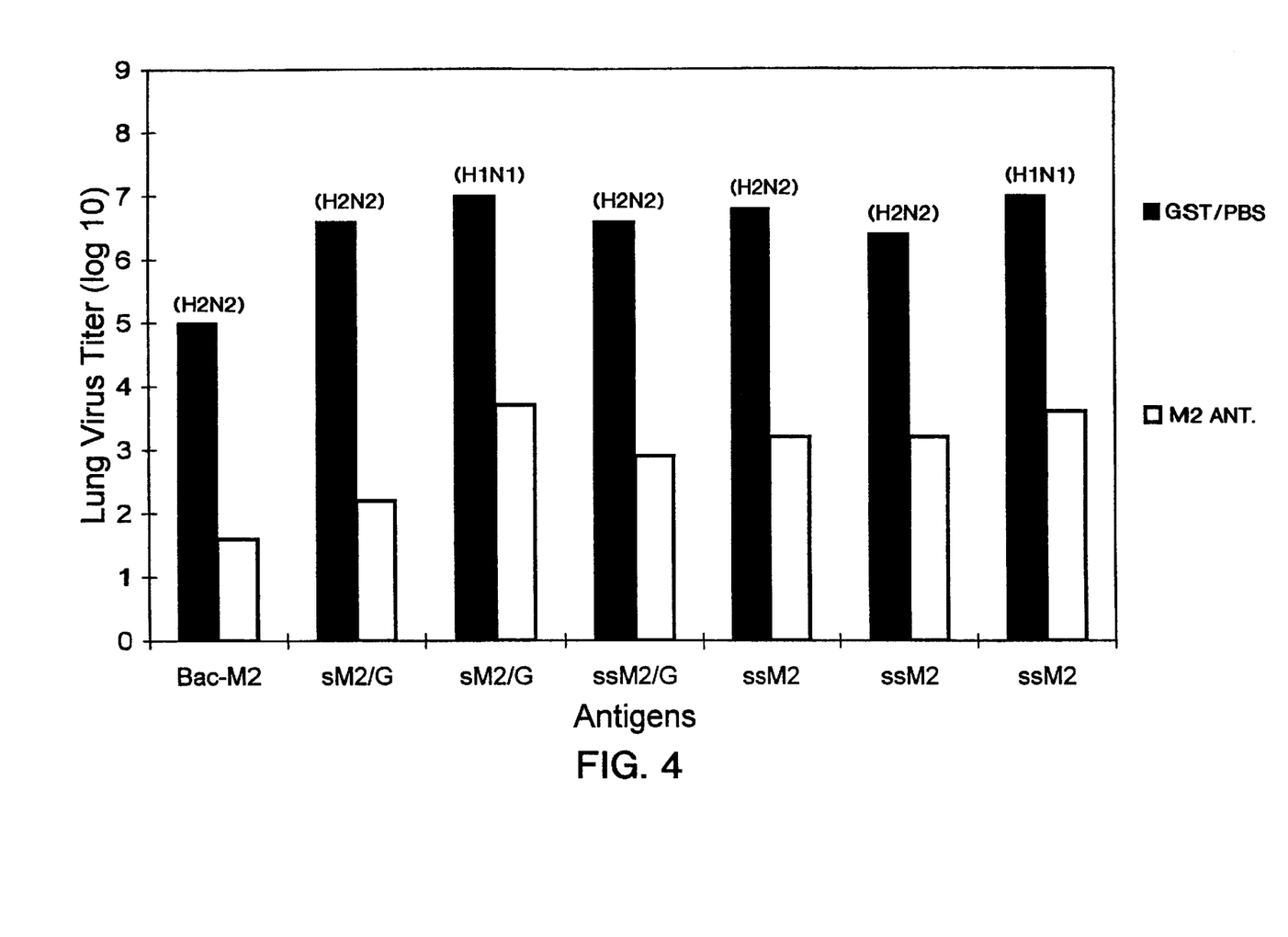
FIG. 4 displays the effect of vaccination of mice with M2 constructs.

Expressed proteins were analyzed for size and purity on an SDS-12%-polyacrylamide gel, followed by staining with Coomassie brilliant blue R-250. FIG. 3(A) shows an SDS-PAGE gel of recombinant proteins. Lanes are: (1) molecular weight markers (2) a sample from the crude bacterial lysate of an induced sM2/G culture (3) a purified sample of GST protein (4) sM2/G protein (6) ssM2 protein which is isolated by cleaving ssM2/G with factor Xa protease. Molecular weights were compared to low molecular weight Rainbow Markers (Amersham International, Arlington Heights, Ill.). For immunoblotting, gels were transferred to Immobilon-P membrane (Millipore, Bedford, Mass.) using a semi-dry transblot apparatus (Bio-Rad, Richmond, Calif.). Membranes were immunoblotted with a 1:5000 dilution of ascitic fluid containing the M2-specific antibody 14C2, followed by labeling with the ECL system (Amersham International, Arlington Heights, Ill.) and exposure to X-ray film. FIG. 3(B) shows a Western blot of GST, sM2/G and ssM2/G using 14C2 as the primary antibody.

EXAMPLE 4

Animal Vaccination and Challenge

Fusion proteins or control GST protein were added to equal volumes of PBS and incomplete Freund's adjuvant. A volume of 0.2 ml, containing 10 vg of protein was injected intraperitoneally (i.p.) into female BALB/c mice, aged 6–12 weeks. Boosts were given after 3 and 6 weeks for a total of 3 inoculations. Animals were bled from the orbital plexus at weeks 6 and 9 and individual sera were tested for antibodies which would react with a synthetic peptide composed of the first 17 amino acids of M2 (peptide $PM_2$-1, Slepushkin et al., 1995). Antibody binding was detected on peptide-coated ELISA plates by adding horseradish peroxidase-conjugated anti-mouse Ig and o-phenylenediaminehydrochloride and hydrogen peroxide as colorimetric substrates. Titers are expressed as the highest dilution which yielded an optical density $(OD)_{490}$ two times higher than a similarly diluted control sera.

Following inoculations, mice were subjected to sub-lethal challenge by heterologous influenza A virus. Mice were anesthetized with $CO_2$ and were infected intranasally (i.n.) with 100 mouse infectious doses $(MID)_{50}$ of MA A/Ann Arbor/6/60 (H2N2) virus or A/Taiwan/1/86 (H1N1) [equivalent to $5.3 \times 10^6$ and $1.3 \times 10^5$ egg infectious doses $(EID)_{50}$ respectively] in a volume of 50 vl of PBS. Mice were euthanized seven days after challenge. Lung homogenates were prepared and titrated into embryonated eggs for virus infectivity. Statistical significance of the data was determined using the Fisher exact test or Student's t test.

EXAMPLE 5

Expression of Recombinant M2 and M2 Transmembrane Deletants

Figure 2:
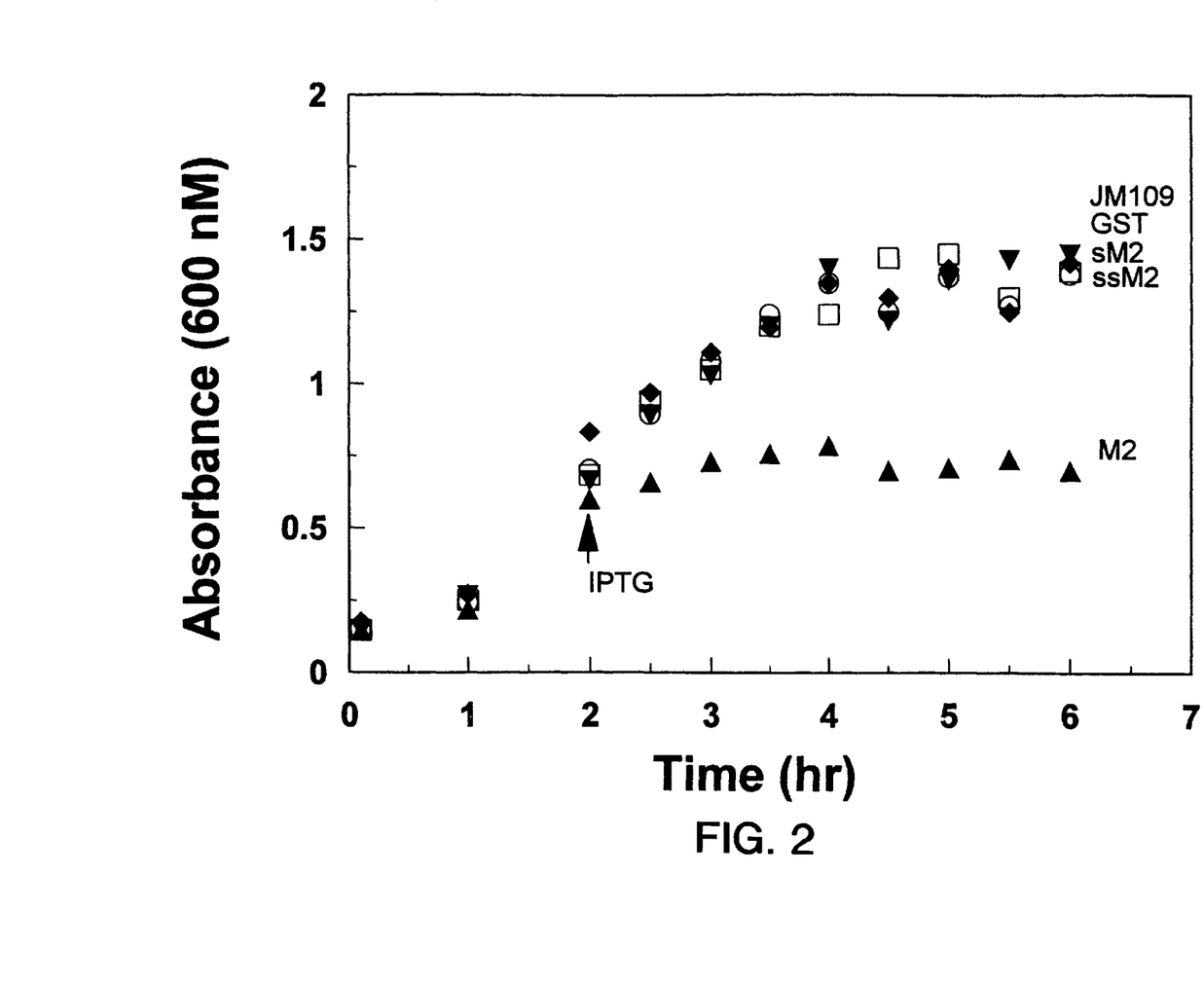
FIG. 2 represents growth curves showing the time course of cell replication and expression of full-length and variant M2 polypeptides.

The effects of expression of GST-fusion M2/G, sM2/G, ssM2/G, and GST on cell viability was tested at various times following induction of *E. coli* JM109 cells containing the respective pGEX constructs (FIG. 2). Overnight cultures were diluted 1:100, reamplified for 2 hrs, and then induced with IPTG. At the time of induction the density of the M2/G culture was consistently lower than other cultures, presumably due to basal expression of the protein. The density of cells expressing full-length M2/G rose only marginally after induction, consistent with the reported lytic properties of M2 when expressed in *E. coli* (Guinea and Carrasco, 1994). Addition of 5 vM amantadine to the culture media did not accelerate this growth pattern, and little, if any, M2/G fusion protein was obtainable from these cultures. In comparison, cultures of sM2/G and ssM2/G maintained a robust pattern of growth comparable to that of the control culture and the GST control protein.

The first deletion construct, which removes the transmembrane domain of M2 (sM2/G, residues 26–43), although expressing well, yielded no purified fusion protein with a standard lysis protocol, suggesting that it remained insoluble or in aggregated form. Adopting the sarkosyl protocol produced a modest yield of ~3 mg of fusion protein/L of bacterial culture, as determined by Bradford protein assay. Further deletion, from residue 26 to 56 (ssM2/G), was found to substantially improve fusion protein yield without the sarkosyl procedure, suggesting a soluble product. Residues 44–56 of mature M2 are all hydrophobic and contribute to a positive hydrophobic index for M2 in Kyte-Doolittle analysis (Lamb et al., 1985). Thus, improved solubility and concomitantly greater yield of this variant M2 polypeptide are not unexpected. Values of up to 15 mg/L of culture are routinely achieved, with the purity of the fusion proteins in either preparation being >90%.

EXAMPLE 6

SDS-PAGE and Western Blot

GST and fusion proteins were electrophoresed on polyacrylamide gels and either stained with Coomassie blue or prepared for immunoblotting. In FIG. 3(A) a Coomassie stained gel is shown. A total protein sample from induced cells taken in the initial phase of the lysate is included (lane 2). GST (lane 3), from an induction of pGEX without M2 insert, is observed as a 29 kDa protein. Fusion proteins, sM2/G (lane 4) and ssM2/G (lane 5) are found at approximately 43 kDa. Panel (B) shows proteins run on a gel simultaneously with (A), transferred to Immobilon-P membrane, and immunoblotted with M2-specific antibody 14C2. Proteins with an approximate weight of 43 kDa reacted with 14C2. GST is not visualized in the blot. Together, these results suggest that the 14C2 antibody epitope of the M2 deletion proteins is not obstructed by the fusion construction and that 14C2 is binding exclusively to the M2 domain.

EXAMPLE 7

Immunogenic and Protective Properties of Recombinant Fusion Proteins

The immunogenicity and protective efficacy of several M2 constructs were tested by vaccinating groups of BALB/c mice with sM2/G, ssM2/G, and enzymatically isolated ssM2 recombinant proteins. GST peptide was administered as a control. Results are shown in Table 1.

TABLE 1

Virus challenge of mice vaccinated with M2 constructs

| Expt. | Vaccine | n | Serum antibody titer[a] | Lung virus titer[b] |
|---|---|---|---|---|
| 1 | GST | 7 | <50 | 6.5 ± 0.6 (AA/60) |
| 2 | GST | 5 | <50 | 6.6 ± 0.9 " |
| 3 | PBS | 5 | <50 | 6.8 ± 0.4 " |
| 1 | sM2/G | 7 | 152,054 | 2.6 ± 0.6 " |
| 2 | sM2/G | 5 | 19,390 | 2.2 ± 1.5 " |
| 2 | ssM2/G | 5 | 11,138 | 2.9 ± 1.4 " |
| 3 | ssM2 | 7 | 123,838 | 3.2 ± 0.7 " |
| 4 | PBS | 4 | <50 | 7.4 ± 0.7 (AA/60) |
| 4 | GST | 5 | <50 | 6.4 ± 0.6 " |
| 4 | PBS | 3 | <50 | 7.0 ± 0.6 (TW/86) |
| 4 | GST | 6 | <50 | 7.0 ± 1.0 " |
| 4 | sM2/G | 5 | 131,825 | 3.0 ± 0.8 (AA/60) |
| 4 | sM2/G | 6 | 131,825 | 3.7 ± 0.5 (TW/86) |
| 4 | ssM2 | 5 | 1,202,264 | 3.2 ± 1.2 (AA/60) |
| 4 | ssM2 | 6 | 1,202,264 | 3.6 ± 0.5 (TW/86) |

Challenge viruses were mouse adapted A/AA/6/60 (H2N2) and A/Taiwan/1/86 (H1N1).
All vaccinations were 3 × 10 μg of antigen, in Incomplete Freund's adjuvant.
[a]Titers are expressed as the highest dilution of sera having a mean (OD)$_{490}$ greater than the mean plus two standard deviations of similarly diluted control sera.
[b]Mean $\log_{10}$ EID$_{50}$/ml ± SD. Values for all virus titer reductions were significantly lower than control groups by Students t-test ($p < 0.001$).

Groups of 5 to 7 mice were vaccinated as described above and analyzed for serum antibody which could recognize a synthetic peptide designed to mimic the extracellular domain of M2. Sera from mice vaccinated with GST control peptide showed no detectable (<50) antibody titer in any samples prior to challenge. However, groups vaccinated with sM2/G, ssM2/G, and ssM2 proteins showed elevated titers after two inoculations and a third inoculation boosted the mean serum antibody titers for each group substantially. Surprisingly, deletion of the transmembrane region and additional hydrophobic residues of M2 does not appear to alter the immunological properties of the variant polypeptide, making such variant polypeptides suitable candidates for vaccines.

For virus challenge, mice vaccinated with either GST, sM2/G, ssM2/G, or ssM2 were challenged with heterologous MA A/Ann Arbor/6/60 (H2N2) or A/Taiwan/1/86 (H1N1) virus 4 weeks after their final boost. After 7 days the mice were euthanized, and lungs were harvested. Lung virus titers for the sM2/G and ssM2/G fusion protein groups, and isolated ssM2, were over 1000-fold lower than the PBS or GST protein control groups (Table 2). No significant difference was found between the sM2/G, ssM2/G, and ssM2 protective effect. This trend demonstrates a potential of the altered M2 peptides to protect against virus challenge, as has been shown for full-length baculovirus M2. Immunogenic compositions, suitable to be used as vaccines, may be prepared from immunogenic M2 as disclosed herein. Preferably, the antigenic material is extensively dialyzed to remove undesired small molecular weight molecules and/or lyophilized for more ready formulation into a desired vehicle. The immunogenic composition elicits an immune response which produces antibodies, including M2 antibodies which may inhibit viral replication, and also influenza A virus-specific cell-mediated immune responses.

Immunogenic compositions including vaccines may be prepared as injectables, as liquid solutions, suspensions or emulsions. The active immunogenic ingredient or ingredients may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric routes. Alternatively, other modes of administration including suppositories and oral formulations may be desirable. For suppositories, binders and carriers may include, for example, polyalkalene glycols or triglycerides. Such suppositories may be formed from mixtures containing the active ingredient(s) in the range of about 0.5 to about 10%, preferably about 1 to 2%. Oral formulations may include normally employed incipients such as, pharmaceutical grades of saccharine, cellulose and magnesium carbonate. These compositions can take the form of solutions, suspensions, tablets, pills, capsules, sustained release formulations or powders and contain about 1 to 95% of the active ingredient(s), preferably about 20 to about 75%.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, the degree of protection desired, and if needed, to produce a cell-mediated immune response. Precise amounts of active ingredient required to be administered depend on the judgment of the practitioner. However, suitable dosage ranges are readily determinable by one skilled in the art and may be of the order of micrograms of the active ingredient(s) per vaccination. Suitable regimes for initial administration and booster doses are also variable, but may include an initial administration followed by subsequent administrations. The dosage may also depend on the route of administration and will vary according to the size of the host.

The concentration of the active ingredient protein in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LIPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 32) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long-chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. reported that octadecyl esters of aromatic amino acids complexed with a recombinant hepatitis B surface antigen, enhanced the host immune responses against hepatitis B virus.

The choice of adjuvant or combination of adjuvants is entirely within the skills of the ordinarily skilled immunologist. The adjuvants discussed above included adjuvants useful in experimental settings as well as adjuvants of potential human or veterinary application. The influenza A vaccines of the invention can be formulated using any of the aforementioned adjuvants and as such the use of any of the adjuvants in combination or in conjunction with the variant M2 polypeptides of the invention is contemplated by and is thus within the scope of the present invention.

The protocols and discussion provided above are sufficient to enable skilled workers in the field to reproduce the claimed inventions. The present inventors supplement the disclosure by listing scientific publications pertinent to the protocols and materials used to convey the present invention.

REFERENCES

Banerji, J. L. et al., (1983) Cell 33:729.

Black, R. A., Rota, P. A., Gorodkova, N., Cramer, A., Klenk, H. D. & Kendal, A. P. (1993) Production of the M2 protein of influenza A virus in insect cells is enhanced in the presence of amantadine. *Journal of General Virology* 74, 1673–1677.

Black, R. A., Rota, P. A., Gorodkova, N., Klenk, H. D. & Kendal, A. P. (1993) Antibody response of M2 protein of influenza A virus expressed in insect cells. *Journal of General. Virology* 74, 143–146.

Bolivar, et al., (1977) Gene 2: 95.

Brophy, P. M. & Pritchard, D. I. (1994) Parasitic helminth glutathione s-transferases: an update on their potential as targets for immuno- and chemotherapy. *Experimental Parasitology* 79, 89–96.

Brown, et al. (1979). Methods in Enzymology, Academic Press, N.Y., Vol. 68, pgs. 109–151.

Carter P., (1990) Site Specific Proteolysis of Fusion Proteins, Ch. 13 in *Protein Purification: From Molecular Mechanisms to Large Scale Processes*, American Chemical Soc., Washington, D.C.

Chang, et al., (1978) Nature, 275:615.

Ciampor, F., Thompson, C. A., Grambas, S. & Hay, A. J. (1992b) Regulation of pH by the M2 protein of influenza A viruses. *Virus Research* 22, 247–258.

Cox, N. J. & Bender, C. A. (1995) The molecular epidemiology of influenza viruses. *Seminars in Virology* 6, 359–370.

Epstein, S. L., Misplon, J. A., Lawson, C. M., Subbarao, E. K., Connors, M. & Murphy, B. R. (1993) β 2-microglobulin-deficient mice can be protected against influenza A infection by vaccination with vaccinia-influenza recombinants expressing hemagglutinin and neuraminidase. *Journal of Immunology* 150, 5484–5493.

Fiers, et al., (1978) Nature, 273:113.

Fikrig, E., Barthold, S. W., Kantor, F. S. & Flavell, R. A. (1990) Protection of mice against the lyme disease agent by immunizing with recombinant OspA. *Science* 250, 553–555.

Frangioni, J. V. & Neel, B. G. (1993) Solubilization and purification of enzymatically active glutathione s-transferase pGEX fusion proteins. *Analytical Biochemistry.* 210, 179–187.

Goeddel, et al., (1979) Nature 281:544.

Graham, F. L. et al. (1977) J. Gen Virol. 36:59–72, Virology 77:319–329, Virology 86:10–21.

Grambas, S. & Hay, A. J. (1992) Maturation of influenza A virus hemagglutinin-estimates of the pH encountered during transport and its regulation by the M2 protein. Virology 190, 11–18.

Guinea, R. & Carrasco, L. (1994) Influenza virus M2 protein modifies membrane permeability in *E. coli* cells. *FEBS Letters* 343, 242–246.

Holsinger, L. J., Shaughnessy, M. A., Micko, A., Pinto, L. H. & Lamb, R. A. (1995) Analysis of the posttranslational modifications of the influenza virus M2 protein. *Journal of Virology* 69, 1219–1225.

Hughey, P. G., Roberts, P. C., Holsinger, L. J., Zebedee, S. L., Lamb, R. A. & Compans, R. W. (1995) Effects of antibody to the influenza A virus M2 protein on M2 surface expression and virus assembly. *Virology* 212, 411–421.

Ito, T., Gorman, O. T., Kawaoka, Y., Bean, W. J. & Webster, R. G. (1991) Evolutionary analysis of the influenza A virus M gene with comparison of the M1 and M2 proteins. *Journal of Virology* 65, 5491–5498.

Jacob, C. O., Leitner, M., Zamir, A., Salomon, D. & Arnon, R. (1985) Priming immunization against cholera toxin and *E. coli* heat-labile toxin by a cholera toxin short peptide-beta-galactosidase hybrid synthesized in *E. coli. Embo Journal* 4, 3339–3343.

Jakeman, K. J., Smith, H. & Sweet, C. (1989) Mechanism of immunity to influenza: maternal and passive neonatal protection following immunization of adult ferrets with a live vaccinia-influenza virus hemagglutinin recombinant but not with recombinants containing other influenza virus proteins. *Journal of General Virology* 70, 1523–1531.

Johnson, K. S., Harrison, G. B. L., Lightowlers, M. W., O'Hoy, K. L., Cougle, W. G., Dempster, R. P., Lawrence, S. B., Vinton, J. G., Heath, D. D. & Rickard, M. D. (1989) Vaccination against ovine cysticercosis using a defined recombinant antigen. *Nature* 338, 585–587.

Jones (1977), Genetics 85:12.

Katz, J. M., Black, R. A., Rowe, T., Slepushkin, V. A. and Cox, N. J. (1996). Immune mechanisms of protection induced by vaccination of Balb/c mice with influenza A virus M2 protein, pp. 837–43, In: Options for the Control of Influenza III, (L. E. Brown, A. W. Hampson, R. G. Webster, eds.), Elsevier Science, Amsterdam.

Kingsman, et al., (1979) Gene 7:141.

Kleid, D. G., Yansura, D., Small, B., Dowbenko, D., Moore, D. M., Grubman, M. J., McKercher, P. D., Morgan, D. O., Robertson, B. H. & Bachrach H. L. (1981) Cloned viral protein vaccine for foot-and-mouth disease: responses in cattle and swine. *Science* 214, 1125–1129.

Laimins, L. et al., (1981) PNAS 78:993.

Lamb, R. A., Zebedee, S. L. & Richardson, C. D. (1985) Influenza virus M2 protein is an integral membrane protein expressed on the infected cell surface. Cell 40, 627–633.

Ling, I. T., Ogun, S. A. & Holder, A. A. (1994) Immunization against malaria with a recombinant protein. *Parasite Immunology* 16, 63–67.

Lusky, M. L., et al., (1983) Mol. Cell Bio. 3:1108.

MacIntyre, et al., (1987) J.Biol.Chem. 262:8416–8422.

Maniatis, et al. (1989). *Molecular Cloning: A Laboratory Manual*, Cold Spring Harbor Press, Cold Spring Harbor Laboratory, Cold Spring Harbor, N.Y.

Mulligan, R. C. and Berg, P. (1980) Science 209:1422.

Nixon-George et al.

Osborne, T. F., et al., (1984) Mol. Cell Bio. 4:1293.

Shimbo, K., Brassard, D. L., Lamb, R. A. & Pinto, L. H. (1996) Ion selectivity and activation of the M2 Ion channel of influenza virus. *Biophysical Journal* 70, 1335–1346.

Slepushkin, V. A., Katz, J. M., Black, R. A., Gamble, W. C., Rota, P. A. & Cox, N. J. (1995) Protection of mice against influenza A virus by vaccination with baculovirus expressed M2 protein. *Vaccine* 15, 1399–1402.

Smith, D. B. & Johnson, K. S. (1988) Single-step purification of polypeptides expressed in *Escherichia coli* as fusions with glutathione s-transferase. *Gene* 67, 31–40.

Southern P. and Berg, P., (1982) J. Molec. Appl. Genet. 1: 327. Stinchcomb, et al., (1979) Nature 282:39.

Srivastava, A. K., Morita, K., Matsuo, S., Tanaka, M. & Igarashi, A. (1991) Japanese encephalitis virus fusion protein expressed in *Escherichia coli* confers protective immunity in mice. *Microbiological Immunology* 35, 863–870.

Srivastava, A. K., Putnak, J. R., Warren, R. L. & Hoke, C. H. (1995) Mice immunized with a dengue type 2 virus E and NS1 fusion protein made in *Escherichia coli* are protected against lethal dengue virus infection. *Vaccine* 13, 1251–1258.

Sugden, B. et al., (1985) Mol Cell. Biol. 5:410–413.

Sugrue, R. J., Bahadur, G., Zambon, M. C., Hall-Smith, M., Douglas, A. R. & Hay, A. J. (1990) Specific structural alteration of the influenza hemagglutinin by amantadine. *Embo Journal* 9, 3469–3476.

Summers, R. G., et al. (1989) J.Biol.Chem. 264:20082–20088.

Tosteson, M. T., Pinto, L. H., Holsinger, L. J. & Lamb, R. A. (1994) Reconstitution of the influenza virus M2 channel in lipid bilayers. *Journal of Membrane Biology* 142, 117–126.

Treanor, J. J., Tierney, E. L., Zebedee, S. L., Lamb, R. A. & Murphy, B. R. (1990) Passively transferred monoclonal antibody to the M2 protein inhibits influenza A virus replication in mice. *Journal of Virology* 64, 1375–1377.

Tschemper et al., (1980) Gene 10:157.

von Heijne, G. (1990) J. Membrane Biol. 115: 195–201.

Wilson, I. A. & Cox, N. J. (1990) Structural basis of immune recognition of influenza hemagglutinin. *Annual Reviews in Immunology* 8, 737–771.

Yamane, K., et al. (1988) J.Biol.Chem. 263:19690–19696.

Zebedee, S. L. & Lamb, R. A. (1988) Influenza A virus M2 protein: monoclonal antibody restriction of virus growth and detection of M2 in virions. *Journal of Virology* 62, 2762–2772.

We claim:

1. A DNA sequence encoding a variant M2 polypeptide of influenza A, the DNA sequence having a deletion corresponding to amino acids 26 to 43, such that the variant M2 polypeptide encoded by the DNA sequence has reduced hydrophobicity relative to full-length M2.

2. The sequence of claim 1 in a vector suitable for expressing the nucleic acid.

3. The vector of claim 2 in a host suitable for expressing the nucleic acid.

4. The host of claim 3, wherein the host is *E. coli.*

5. A DNA sequence encoding a variant M2 polypeptide of influenza A, the DNA sequence having a deletion corresponding to amino acids 26 to 43, such that the variant M2 polypeptide encoded by the DNA sequence has greater solubility in aqueous buffers than does full-length M2.

6. The sequence of claim 5 in a vector suitable for expressing the nucleic acid.

7. The vector of claim 6 in a host suitable for expressing the nucleic acid.

8. The host of claim 7, wherein the host is *E. coli.*

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 62 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: NO

(iv) ANTI-SENSE: NO

(viii) POSITION IN GENOME:
      (C) UNITS: bp    (xi) SEQUENCE DESCRIPTION: SEQ ID NO:1:

CCCGAATTCT TATGAGCCTT CTAACCGAGG TCGAAACGCC TATCAGAAAC GAATGGGGAT     60

GC     62

(2) INFORMATION FOR SEQ ID NO:2:

(i) SEQUENCE CHARACTERISTICS:
      (A) LENGTH: 52 base pairs
      (B) TYPE: nucleic acid
      (C) STRANDEDNESS: single -continued (D) TOPOLOGY: linear (ii) MOLECULE TYPE: DNA (genomic)

(xi) SEQUENCE DESCRIPTION: SEQ ID NO:2:

GTCTTTGCTT ACCCCTACGT CTACGTTGCT AAGTTCACTA GGACCTCCTC CC    52

(2) INFORMATION FOR SEQ ID NO:3:

(i) SEQUENCE CHARACTERISTICS:
       (A) LENGTH: 41 base pairs
       (B) TYPE: nucleic acid
       (C) STRANDEDNESS: single
       (D) TOPOLOGY: linear    (ii) MOLECULE TYPE: DNA (genomic)

(xi) SEQUENCE DESCRIPTION: SEQ ID NO:3:

CAAGTGATCC TGGAGGAGGA GATCGTCTCT TCTTCAAATG C    41

(2) INFORMATION FOR SEQ ID NO:4:

(i) SEQUENCE CHARACTERISTICS:
       (A) LENGTH: 43 base pairs
       (B) TYPE: nucleic acid
       (C) STRANDEDNESS: single
       (D) TOPOLOGY: linear    (ii) MOLECULE TYPE: DNA (genomic)

(xi) SEQUENCE DESCRIPTION: SEQ ID NO:4:

CAAGTGATCC TGGAGGAGGA AAACACGGTC TGAAAAGAGG GCC    43

(2) INFORMATION FOR SEQ ID NO:5:

(i) SEQUENCE CHARACTERISTICS:
       (A) LENGTH: 41 base pairs
       (B) TYPE: nucleic acid
       (C) STRANDEDNESS: single
       (D) TOPOLOGY: linear    (ii) MOLECULE TYPE: DNA (genomic)

(xi) SEQUENCE DESCRIPTION: SEQ ID NO:5:

CTATCAGTAA AGCAGTCGTA TCTCGACCTC ATCAGCTGCC C    41